United States Patent [19]

Zuckerman

[11] Patent Number: 5,672,610

[45] Date of Patent: Sep. 30, 1997

[54] METHODS OF INCREASING MACROPHAGE FUNCTION

[75] Inventor: Steven H. Zuckerman, Indianapolis, Ind.

[73] Assignee: Eli Lilly and Company, Indianapolis, Ind.

[21] Appl. No.: 170,605

[22] Filed: Dec. 21, 1993

[51] Int. Cl.$^6$ .................. A61K 31/445; A61K 31/40; A61K 31/38
[52] U.S. Cl. ............. 514/324; 514/422; 514/443
[58] Field of Search ............... 514/324, 422, 514/443

[56] References Cited

U.S. PATENT DOCUMENTS

| | | |
|---|---|---|
| 4,133,814 | 1/1979 | Jones et al. . |
| 4,380,635 | 4/1983 | Peters . |
| 4,418,068 | 11/1983 | Jones . |
| 5,075,321 | 12/1991 | Schreiber . |

FOREIGN PATENT DOCUMENTS

| | | |
|---|---|---|
| WO93/10113 | 5/1993 | Japan . |
| WO93/1074 | 6/1993 | WIPO . |

OTHER PUBLICATIONS

Sanders M.C. et al., Hormonal Modulation of Macrophage Clearance of IgG–Sensitized Cells*, Trans. Assoc. Am. Physicians, Vol. 100, pp. 268–275, 1987.

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene" Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB-3 Expression in Bone;" Am. Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol–Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L.J. "Biological Actions and Binding Properties of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio–Breast Cancer Symposium, San Antonio, Texas, Nov. 5–6, 1982.

(List continued on next page.)

Primary Examiner—Zohreh Fay
Attorney, Agent, or Firm—James J. Sales

[57] ABSTRACT

A method of increasing macrophage function comprising administering to a human in need thereof an effective amount of a compound having the formula

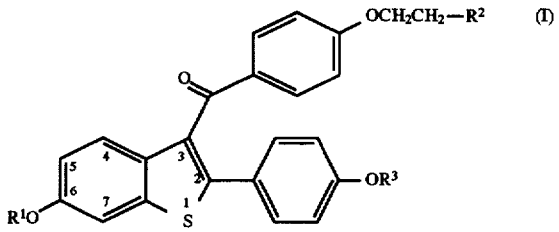

wherein $R^1$ and $R^3$ are independently hydrogen, —$CH_3$,

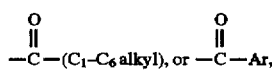

wherein Ar is optionally substituted phenyl;
$R^2$ is selected from the group consisting of pyrrolidine, hexamethyleneamino, and piperidino; or a pharmaceutically acceptable salt of solvate thereof.

Also encompassed by the invention is a method of treating immunocompromissed individuals comprising administering a compound of formula 1.

8 Claims, No Drawings

OTHER PUBLICATIONS

Black et al., The Antiestrogenic Action of LY139481: Species Uniformity Duration of Action and Kinetics of 3H-LY139481 Distribution In Vivo. Sixty-fifth Annual Meeting of the Endocrine Society, San Antonio, Texas, Jun. 8-10, 1983, abs. 93.

Black et al., Antagonism of Estrogen Action with a New benzothiophene Derived Antiestrogen, Life Sciences, 32:1983. 1031-1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1-7, 1984, abs. 323.

Black et al., Synthesis and Antiestrogenic Activity of [3,4-Dihydro-2(4-methoxyphenyl)-1-napthalenyl] [4-[2-pyrrolidinyl) ethoxyl]-phenyl]methanone methanesulfonic acid salt, Journal of Medicinal Chemistry 22;1979, 962-966.

Black et al., Antiestrogens 2. Structure Activity Studies in a Series of 3-Aroyl-2-arylbenzo[b]thiophene Derivatives Leading to [6-Hydroxy-2-(4-hydroxyphenyl)benzo[b]thien-3-yl][4-[2-(1-piperidinyl)ethoxy]-phenyl]methanone Hydrochloride (LY156758), a Remarkably Effective Estrogen Antagonist with Only Minimal Intrinsic Estrogenicity, J. Med. Chem. 27(8), 1984, 1057-1066.

Flynn, *Life Sciences*, 38, 2455-2460, (1986).

Ahmed et al., *Am J Path*, 121(3), 531-551 (1985).

Classen et al., *J Immunol Methods*, 134, 153-161 (1990).

Zuckerman et al., *J Immunol*, 140(3), 978-983, (1988).

Seow et al., *J. Immunol Methods*, 98, 113-118, (1987).

Evans et al., *Circ Shock*, 29, 279-290, (1989).

Nemunaitus, *Transfusion*, 33(1), 70-83 (1993).

Ragsdale et al., *J Immunol Methods*, 123, 259-267 (1989).

Gordon et al., Current Opinion in Immunology, 4, 25-32 (1992).

Fuller, *Br Med Bull*, 48(1), 65-71 (1991).

Freidman et al., *J Clin Invest*, 75, 162-167 (1985).

METHODS OF INCREASING MACROPHAGE FUNCTION

BACKGROUND OF THE INVENTION

Macrophages play a central role in host defense through a variety of effector mechanisms involving both membrane related and secretory events (Gordon et al., *Curr. Opin, Immunol.* 4, 25, 1992; Fuller, *Brit, Med. J.,* 48, 65, 1992). Phagocytosis, chemotaxis and antigen presentation are membrane related processes involved in immunologic defense mechanisms necessary for host survival. The importance of macrophages in defense against microbes, immune surveillance, destruction of tumor cells, and in the clearing of senescent erythrocytes has been documented in man and in animal models characterized by the selective elimination of macrophages (Claassen et al., *J. Immunol Meth,* 134, 153, 1990). Macrophages also contribute to host defense through secretion of bacteriostatic and bactericidal proteins, cytokines and lipid mediators, as well as oxygen and nitrogen reactive intermediates. The secretory capacity of the macrophage is central to its function as these cells secrete over 100 distinct mediators and are located in every organ (Nathan, *J. Clin. Invest.,* 79, 319, 1987).

While aberrant activation of macrophage functions is associated with autoimmune diseases as well as both chronic and acute inflammatory processes, the reciprocal condition, suppression of macrophage effector functions, is associated with reoccurring infections of both opportunistic and non-opportunistic pathogens and contributes to increased morbidity and mortality. Populations associated with an immunocompromised state include burn patients, transplants, HIV infected individuals, cancer patients undergoing chemotherapy and surgical patients, notably those with a higher risk of infection as observed in thoracoabdominal patients.

Current therapeutic approaches to these patients includes the use of intravenous infusion of macrophage derived cytokines notably the colony stimulating factors G-CSF, GM-CSF, and M-CSF (Nemunaitis, Transfusion 33: 70, 1993). Supportive therapy with antibiotics and fluids is also used however the limitations of these approaches are demonstrated by the continued problems of infection in immunocompromised patients and the emergence of more deadly strains of antibiotic resistant organisms. Furthermore, infections of immunocompromised patients with opportunistic pathogens including Pneumocystis and Cryptococcal infections remain significant and result in complications despite various antibiotic protocols. Clearly, novel therapeutics which can selectively enhance macrophage effector functions to augment host defense would play a central role in the clinical management of these patients.

Estrogen has been reported to increase select macrophage effector functions including Fc mediated phagocytosis, class II antigen expression, and IL-1 secretion. These observations coupled with the known propensity of women to be more resistant to a variety of infections (Ahmed et al., *Am, J. Path.,* 12, 531, 1985) suggests that estrogen-like compounds may enhance macrophage effector functions and thus be beneficial in disease states associated with depressed host defense.

SUMMARY OF THE INVENTION

This invention provides methods for increasing macrophage function comprising administering to a human in need thereof an effective amount of a compound of formula I

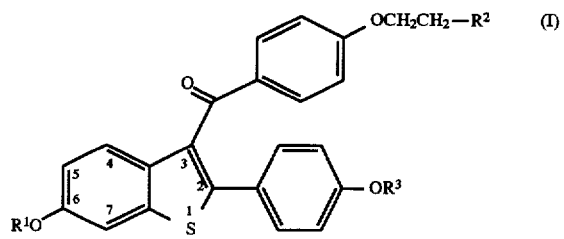

wherein $R^1$ and $R^3$ are independently hydrogen, —CH$_3$,

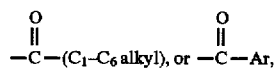

—C—(C$_1$-C$_6$ alkyl), or —C—Ar, wherein Ar is optionally substituted phenyl;

$R^2$ is selected from the group consisting of pyrrolidino, hexamethyleneimino, and piperidino; and pharmaceutically acceptable salts and solvates thereof.

Also encompassed by the invention is a method of treating an immunocompromised human comprising administering a compound of formula I to said human.

DETAILED DESCRIPTION OF THE INVENTION

The current invention concerns the discovery that a select group of 2-phenyl-3-aroylbenzothiophenes (benzothiophenes), those of formula I, are useful for Increasing macrophage function. It is believed the benzothiophenes disclosed increase macrophage function, including class II antigen expression, (hence antigen presentation), Fc mediated phagocytosis, and/or cytokine release. The therapeutic and prophylactic treatments provided by this invention are practiced by administering to a human in need thereof a dose of a compound of formula I or a pharmaceutically acceptable salt or solvate thereof, that is effective to increase macrophage function.

The term "increasing macrophage function" is defined to include enhancement or augmentation of macrophage function or activation rate so as to augment a human's defense.

The compound of formula 1 should be useful in the treatment, both prophylactic and therapeutic, in immunocompromised persons, and in particularly in thoracoabdominal surgical infections, myeloid depressed patients following chemotherapy, burn patients, HIV infected individuals, and transplant patients undergoing immunosuppressive therapy. Additional uses would include prophylactic and therapeutic uses for reoccurent bacterial, protozoan, and fungal infections, as well as in patients with Myelodysplastic syndrome and aplastic anemia in which myeloid cells are largely non-functional. It is anticipated that in any clinical entity in which Colony Stimulating Factors are being used, the compounds of formula 1 would also be useful.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic-mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to increase macrophage function or treat an immunocompromised individual, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively treat or prevent the disease(s) or symptom(s).

It is usually preferred to administer a compound of formula I in the form of an acid addition salt, as is customary in the administration of pharmaceuticals bearing a basic group, such as the piperidino ring. It is preferred to administer a compound of the invention to a female, and further to an aging human (e.g. a post-menopausal female). For such purposes the following oral dosage forms are available.

FORMULATIONS

In the formulations which follow, "Active ingredient" means a compound of formula I.

Formulation 1: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

| Ingredient | Quantity (mg/capsule) |
| --- | --- |
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
| --- | --- |
| Ingredient | Quantity (mg/tablet) |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

| Formulation 7: Tablets | |
| --- | --- |
| Ingredient | Quantity (mg/tablet) |
| Active ingredient | 0.1–1000 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

| Formulation 8: Suspensions | |
| --- | --- |
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Assays

Assay 1

The procedure as set out in Freidman et al., *J. Clin, Invest.*, 75, 162–167 (1985) (herein incorporated by reference) is carried out, with certain modifications. Between five and one hundred mice are administered oral doses in the range of 1–10 mg/kg of a compound of formula 1 on a daily basis. Following the administration, macrophages are harvested and changes in both immune (Fc mediated) and non-immune phagocytosis are quantitated by using fluorescein conjugated yeast particles prepared based on Ragsdale, *J Immunol Meth*, 123:259, (1989). For immune mediated phagocytosis, fluorescein conjugated yeast is preincubated with mouse sera to promote opsonization. Increase in fluorescence uptake by macrophages is quantitated by an increase in fluorescent emission using excitation and emission wavelengths of 482 and 520 nm, respectively. This procedure is used with ex vivo or in vitro macrophage cultures and changes in fluorescence units quantitated.

An increase in fluorescent units, as compared to control indicates activity of compounds of formula 1.

Assay 2

The procedure as set out in Zuckerman et al., *Cell Immunol*, 103:207, (1986); *J Immunol*, 140:978 (1988) (herein incorporated by reference) is carried out. The ability to induce class II antigens and consequently promote antigen presentation is determined on ex vivo primary peritoneal macrophages and in vitro with the murine macrophage cell line P388D1. Between five and one hundred mice are dosed with a compound of formula 1 macrophages are harvested and probed with antibodies against class II antigens of the D haplotype. Increased class II antigen expression is determined by flow cytometry using the appropriate secondary antibodies. In vitro studies evaluate the effects of the compounds in increasing the basal level and gamma interferon inducible expression of class II antigen by flow cytometry. An increase in class II expression reflect an increase in macrophage activation.

Assay 3

The procedure as set out in Seow et al., *J. Immunol. Meth.*, 98, 113 (1987) (herein incorporated by reference) is carried out. The assay is used to evaluate increases in macrophage effector functions which uses measurements of 2-deoxyglucose uptake. Macrophages ex vivo and in vivo are plated in 96 well plates at $10^5$ cells per well and incubated in phosphate buffered saline in the presence of 0.78 uCi/ml of 3H-deoxyglucose, and a compound of formula 1 is placed in the wells. Reduction in the amount of extracellular glucose reflects the uptake of this non-metabolizable glucose analog and consequently provides an independent assay for the determination of the state of macrophage activation mediated by the compound of formula 1. Increase in deoxyglucose uptake by the compound demonstrates the ability of the compounds to increase the state of macrophage activation.

Assay 4

The procedure as set out in Zuckerman, *Circ Shock* 29, 279 (1989) (herein incorporated by reference) is carried out to illustrate the ability of the compounds of formula 1 to protect in murine sepsis and endotoxin lethality models. Between five and one hundred mice are dosed orally with 1-10 mg/kg with a compound of formula 1 for 1 week prior to sepsis challenge. Challenge is performed using a bolus IV endotoxin injection under condition in which an LD100 is achieved (200 µg lipopolysaccharide). Exogenous glucocorticoids such as dexamethasone at 20 mg/kg serve as a positive control in increasing survival. The effects of the compound of formula 1 is also determined using a sepsis model involving cecal ligation and puncture. Sepsis by both Gram positive and Gram negative organisms results in an LD100 by 48 hours despite the use of antibiotics. An increase in the number of surviving animals or in survival time, as compared to control, demonstrates the activity of the compounds.

Assay 5

The ability of the compounds of formula 1 to increase the secretion of cytokines such as TNF is quantitated in vivo by sera measurements using commercially available TNF ELISAs specific for mouse TNF. Between five and one hundred mice are orally dosed with 1-10 mg/kg of a compound of formula 1 for one week prior to injection of a lethal or sublethal dose of lipopolysaccharide (200 and 1 µg, respectively). At one hour post LPS injection the mice are bled and the basal and LPS inducible amounts of serum TNF determined. Routinely, TNF levels below 10 pg/ml are observed prior to LPS injection and achieve levels of 5-20 ng/ml following LPS. The ability of the compounds to modulate the basal or inducible levels of TNF is determined. An increase in basal TNF without triggering massive systemic TNF release in compound treated mice demonstrates the activity of the compounds in promoting cytokyne secretion. Finally, ex vivo and in vitro measurements of TNF release from peritoneal macrophages exposed to 1-5 µM of a compound in vitro is also performed by ELISA to determine the extent of cytokine increase mediated by a compound of formula 1.

Assay 6

Five to fifty women are selected for the clinical study. The women are immunosuppressed. Because of the idiosyncratic and subjective nature of these disorders, the study has a placebo control group, i.e., the women are divided into two groups, one of which receives a compound of formula 1 as the active agent and the other receives a placebo. Women in the test group receive between 50-200 mg of the drug per day. They continue this therapy for 3-12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have in at least one of the assays described above.

We claim:

1. A method of increasing macrophage function so as to augment a humans defense comprising administering to a human in need thereof an effective amount of a compound having the formula

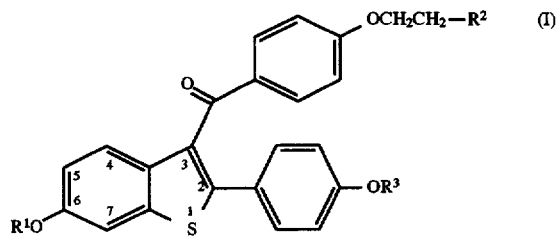

wherein $R^1$ and $R^3$ are independently hydrogen, —CH$_3$,

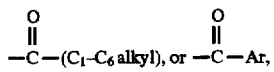

wherein Ar is optionally substituted phenyl;

$R^2$ is selected from the group consisting of pyrrolidine, hexamethylenemino, and piperidino; or a pharmaceutically acceptable salt of solvate thereof.

2. The method of claim 1 wherein said compound is the hydrochloride salt thereof.

3. The method of claim 1 wherein said compound is

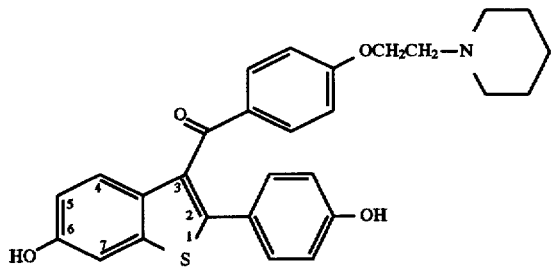

or its hydrochloride salt.

4. The method of claim 1 wherein said human is a post-menopausal woman.

5. The method of claim 1 wherein said human is immunocompromised.

6. The method of claim 5 wherein said human suffers from Myelodysplastic syndrome, aplastic anemia, any physiological condition in which Colony Stimulating Factors could be used, myeloid depression, or is receiving immunosuppressive therapy, or is to undergo a thoracoabdominal surgery, or is a burn patient.

7. A method of treating an immunocompromised human comprising administering to a human in need thereof an effective amount of a compound having the formula

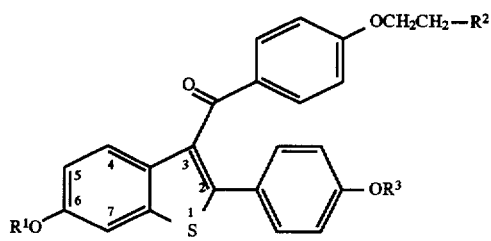
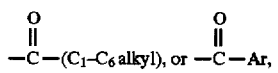
wherein $R^1$ and $R^1$ are independently hydrogen, —$CH_3$,
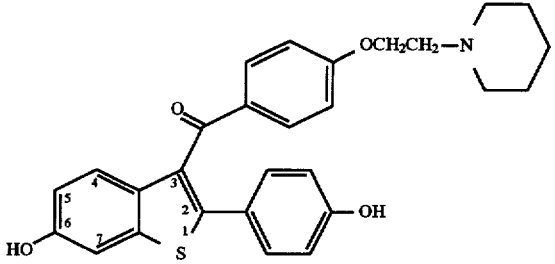
wherein Ar is optionally substituted phenyl;
$R^2$ is selected from the group consisting of pyrrolidine, hexamethylenemino, and piperidino; or a pharmaceutically acceptable salt of solvate thereof.
8. The method of claim 7 wherein said compound is
or its hydrochloride salt.